United States Patent [19]

DeMartini

[11] Patent Number: 4,997,418

[45] Date of Patent: Mar. 5, 1991

[54] EPIDERMAL IONTOPHORESIS DEVICE

[75] Inventor: Richard J. DeMartini, Largo, Fla.

[73] Assignee: C. P. Chambers, Clearwater, Fla. ; a part interest

[21] Appl. No.: 294,878

[22] Filed: Jan. 9, 1989

Related U.S. Application Data

[63] Continuation-in-part of Ser. No. 184,374, Apr. 21, 1988, abandoned.

[51] Int. Cl.$^5$ .............................................. A61N 1/30
[52] U.S. Cl. ..................................................... 604/20
[58] Field of Search .................. 604/20; 128/800, 381, 128/796, 797, 801

[56] References Cited

U.S. PATENT DOCUMENTS

| | | | |
|---|---|---|---|
| 397,474 | 2/1889 | Stanley | 128/800 |
| 2,447,127 | 8/1948 | Landauer | 128/800 |
| 3,107,672 | 10/1963 | Hofmann | 128/798 |
| 4,033,356 | 7/1977 | Hara | 128/798 |
| 4,141,359 | 2/1979 | Jacobsen et al. | 128/419 R |
| 4,406,658 | 9/1983 | Lattin et al. | 128/419 R |

FOREIGN PATENT DOCUMENTS

| | | | |
|---|---|---|---|
| 225556 | 6/1987 | European Pat. Off. | 604/20 |
| 2548029 | 1/1985 | France | 604/20 |
| 2063072 | 6/1981 | United Kingdom | 604/20 |
| 2132892 | 7/1984 | United Kingdom | 604/20 |

Primary Examiner—Kyle L. Howell
Assistant Examiner—Kevin Pontius
Attorney, Agent, or Firm—Herbert W. Larson

[57] ABSTRACT

Iontophoresis device capable of being hand held and activated by thumb contact with a positive electrode and scalp skin contact with a negative electrode. The device has a two component housing enclosing an electrical circuit connecting the two electrodes. The circuit utilizes a 9 V battery, two load regulators, two capacitors, a momentary switch and a 2 V–40 V output range DC/DC converter. Alternatively, negative electrodes of varying structure can be plugged into the device to provide multi-purpose application to the scalp and the positive electrode can be separately plugged to the device to free the hand of the treating technician.

14 Claims, 5 Drawing Sheets

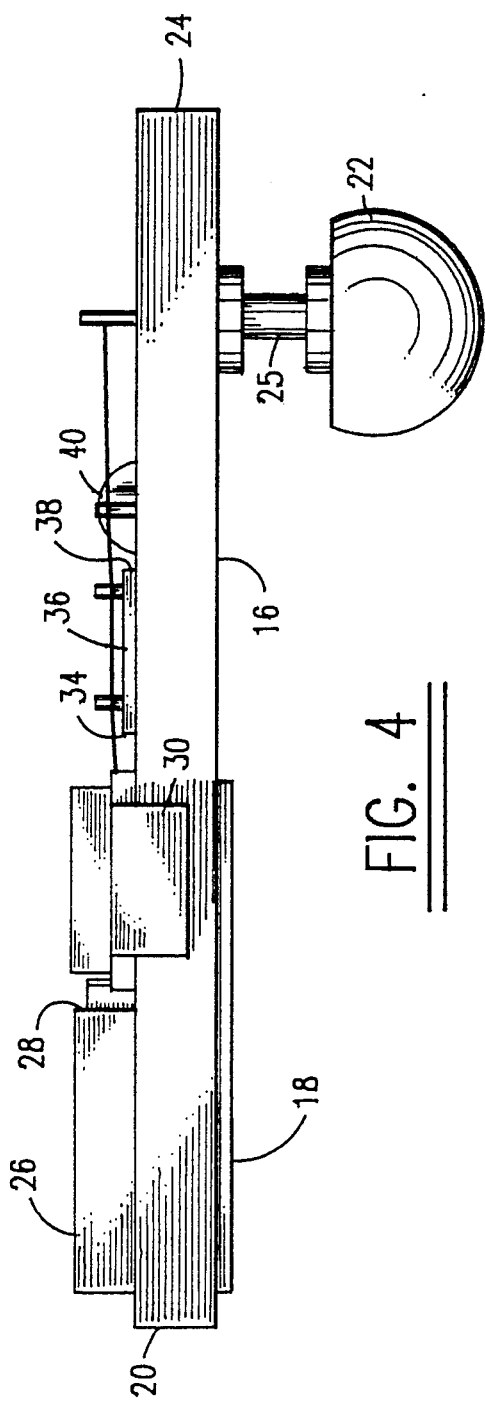
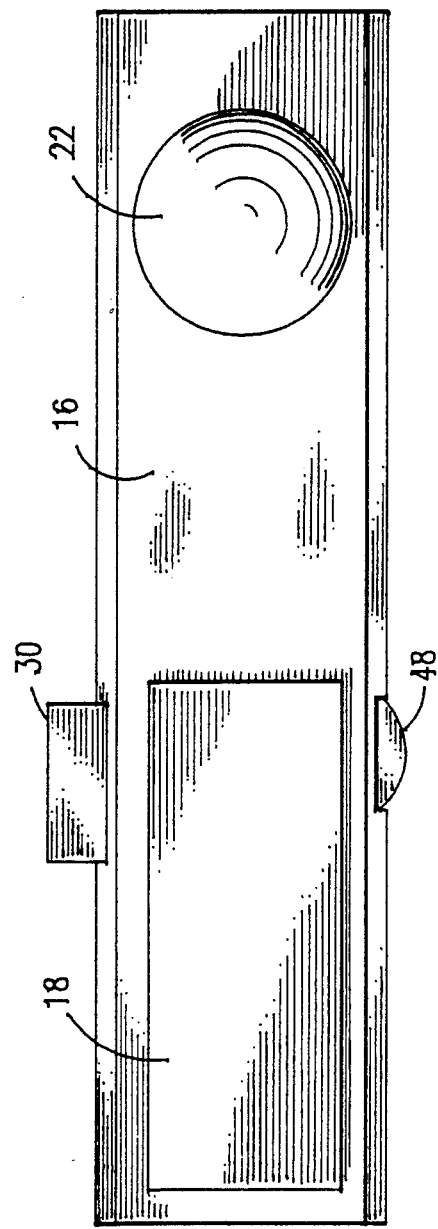

EPIDERMAL IONTOPHORESIS DEVICE

PRIOR APPLICATIONS

This application is a continuation-in-part of my application U.S. Ser. No. 184,374, filed Apr. 21, 1988 now abandoned.

BACKGROUND OF THE INVENTION

1. Field of the Invention

This invention relates to an electrical apparatus and method for facilitating the penetration of topical creams through the epidermis. More specifically, it refers to a hand held electrical apparatus providing an output of highly filtered negative DC current to human skin surfaces to cause vaso-dilation and aid in the penetration of skin cream through the epidermis layer of cells.

2. Description of the Prior Art

Iontophoresis is a term used to describe a Process whereby charged particles penetrate the epidermis by application of direct electrical current to the skin surface. These charged particles produce specific physiochemical reactions in the epidermis tissue. The positively charged sodium ions in solution within the tissue migrate towards the negative pole of the applicator apparatus. The resulting chemical reaction in water forms sodium hydroxide and hydrogen. The sodium hydroxide produces local liquification of epidermis protein and softening of tissue. The negatively charged chlorine ions in solution within epidermis tissue migrates towards the positive pole of the applicator apparatus and forms hydrochloric acid. This local acidification results in coagulation of protein and hardening of tissue. These chemical reactions serve to depolarize the epidermis cell membrane by changing its permeability and thereby allowing topical creams lo penetrate the epidermis more readily.

Utilizing the above principles, many electrical devices have been created to stimulate the absorption of various substances through the epidermis. One such device is described in U.S. Pat. No. 4,141,359. This device employs cumbersome equipment containing a pulse-width modulated DC-DC converter together with feedback circuitry and a safety cut-off circuit. U.S. Pat. No. 4,301,794 describes a method of periodically reversing the current and conducting a short pulse of current through the skin in the opposite direction while a patient is undergoing iontophoretic treatment. U.S. Pat. No. 4,406,658 describes an iontophoretic device having a means of switching electrode polarity so that greater amounts of the ionic substance can be delivered in a single application. U.S. Pat. No. 4,340,047 describes an apparatus conducting direct current through the skin with short pulses in an opposite direction. U.S. Pat. No. 4,655,232 describes a method of electrically heating skin with a flat aluminum disk while applying a lotion to the skin and massaging the skin surface with the disk. U.S. Pat. No. 3,107,672 describes an applicator with a battery operated conductive sponge member on the applicator. Other references which relate to applying electrical stimulation to the skin are U.S. Pat. Nos. 3,424,165; 3,601,126; 4,033,356; 4,532,938; and 4,619 252. In addition my previous application U.S. Ser. No. 120,920, now abandoned, filed Nov. 16 1987, relates to a pulse device for a facial skin applicator.

Although the above devices accomplish their intended purpose there is no simple hand held mini-apparatus employing a DC/DC converter that can be easily employed by an individual to allow for his or her self application of a skin cream.

SUMMARY OF THE INVENTION

I have invented mini vaso controller apparatus for application of creams through epidermis tissue. My apparatus is simple to use by an individual without assistance.

My apparatus employs top and bottom housing members enclosing a nine volt battery, an on/off momentary switch, an output control knob, two 470 microfarad capacitors, a DC/DC converter and an applicator head mounted on the exterior of one housing member together with a positive pole thumb contact in the form of an electrode strip. The negative DC current/voltage field around the applicator head is applied to a scalp area to cause vaso dilation. The positive base electrode is contacted on the thumb by the individual to complete the circuit from thumb to scalp. Alternatively, the negative electrode can vary in shape and can be plugged into the apparatus housing. The positive electrode can also be separate component plugged into the housing.

BRIEF DESCRIPTION OF THE DRAWINGS

The invention may be best understood by those having ordinary skill in the art by reference to the following detailed description when considered in conjunction with the accompanying drawings in which:

FIG. 4 is a right side view in elevation with the top housing removed.

FIG. 6 is a bottom plan view of the applicator.

DETAILED DESCRIPTION OF THE INVENTION

Figure 1:
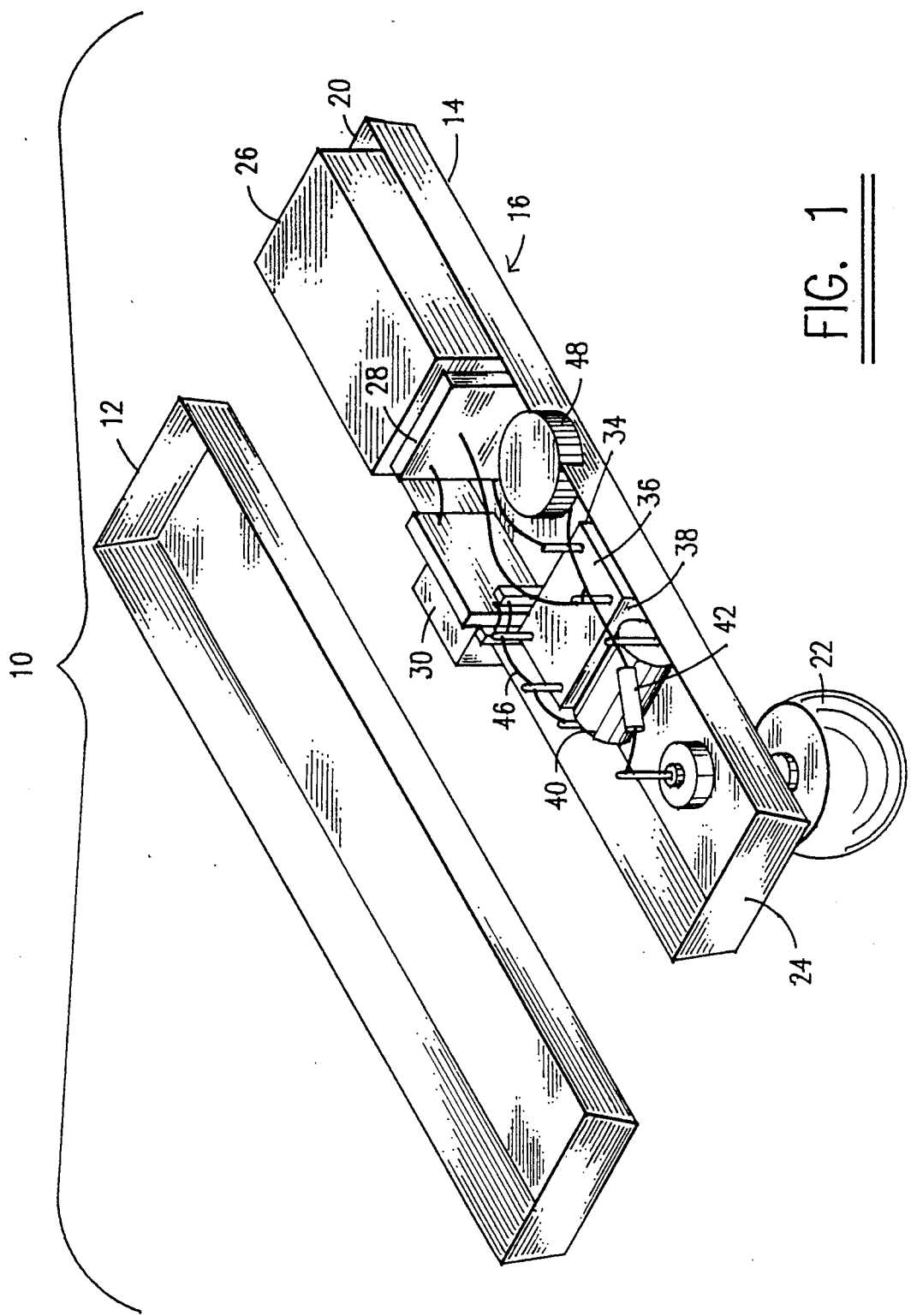
FIG. 1 is a perspective view of the applicator with its top housing separated from the base housing.
Figure 2:
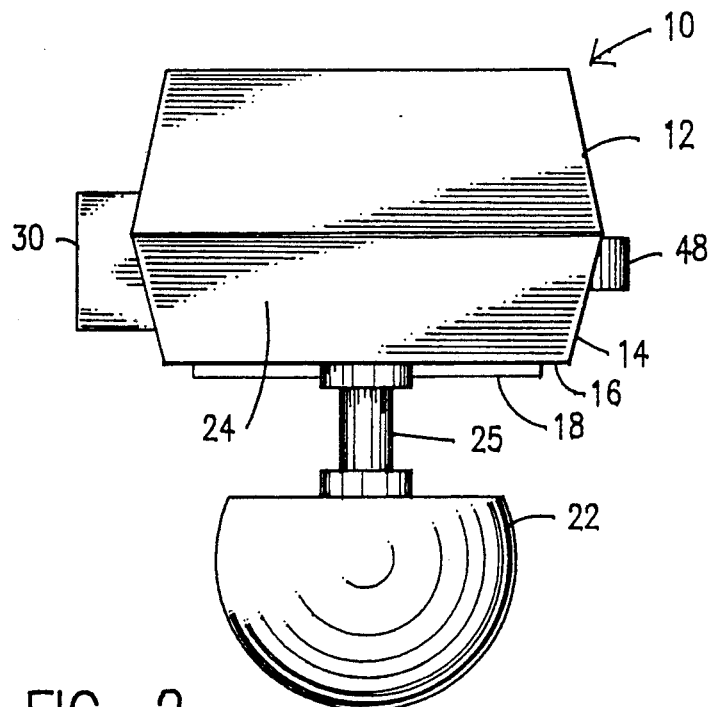
FIG. 2 is a front view in elevation of the applicator.
Figure 3:
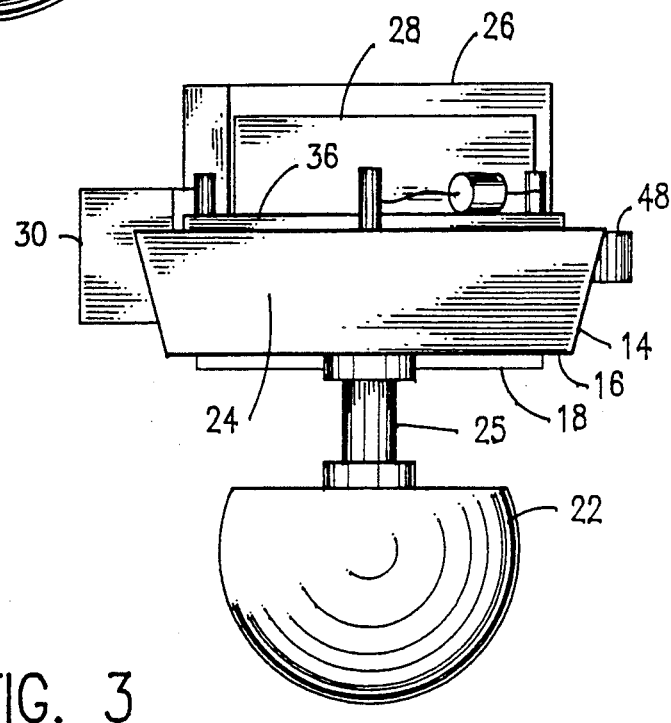
FIG. 3 is a front view in elevation with the top housing removed.
Figure 7:
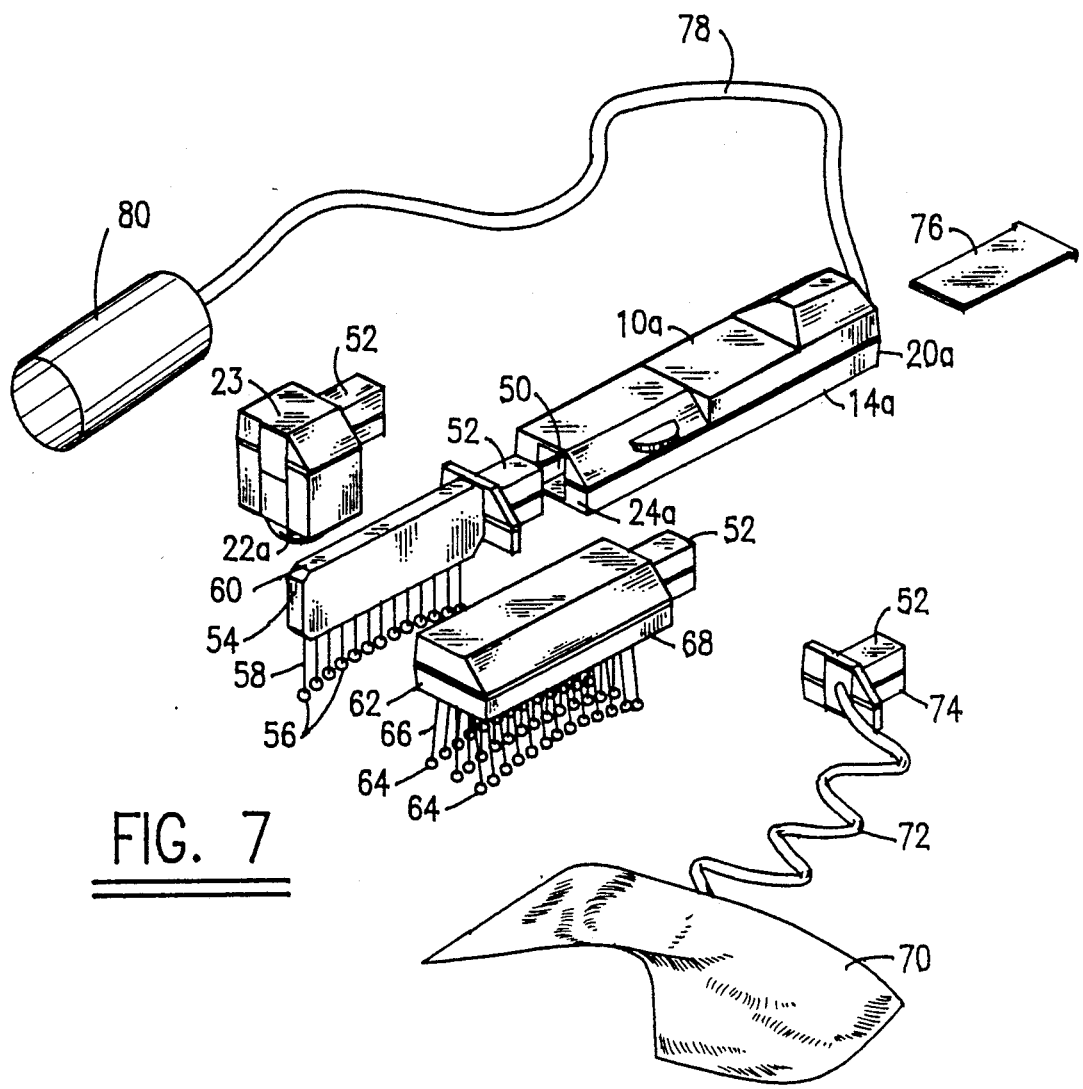
FIG. 7 is a perspective view of an alternate apparatus of this invention with variable design negative electrodes pluggable to the apparatus.

Throughout the following detailed description the same reference numerals refer to the same elements in all figures. The mini vaso controller apparatus 10 shown in FIG. 1 has an upper housing shell 12 and a lower housing shell 14 that snap together. The lower housing shell has mounted on the underside 16, a positive electrode 18 at a first end 20 and a negative electrode 22 at a second end 24. A short stem 25 connects the electrode 22 to the housing shell 14.

The electrode 18 is capable of being engaged by a thumb. The negative electrode 22 is an applicator head.

Figure 5:
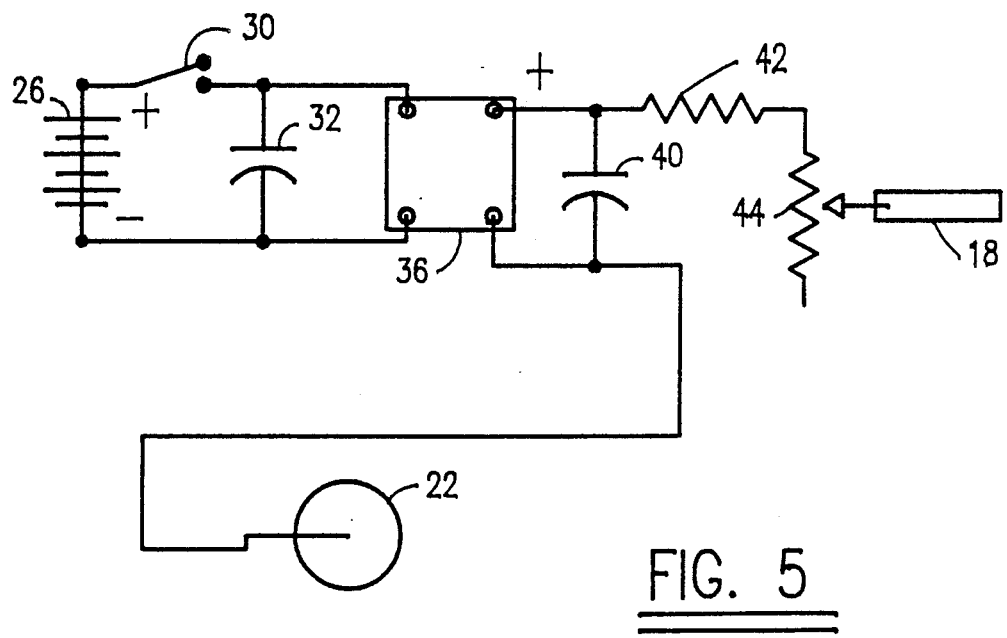
FIG. 5 is a schematic of the applicator's electrical system.

The two electrodes are connected by an electrical circuit shown in the schematic of FIG. 5 to have a nine volt battery 26 mounted at the first end 20 of the housing shell 14 and held in place by a battery clip 28.

An on/off momentary switch 30 is capable of breaking the circuit. The switch is kept in a normally open position. A typical switch is a single pole single throw type.

A first 470 microfarad capacitor 32 is connected at a first end 34 to a 9 to 48 volt DC to DC converter 36. At the second end 38 of the DC/DC converter 36 a second optional 470 microfarad capacitor 40 is located in the circuit.

A first optional load regulator resistor 42 having a 3.3–10K ohm resistance and a second variable load regulator resistor 44 having up to about a 50K ohm resistance serving as a gain control is added to the circuit to adjust output sensitivity. Resistor 44 is connected to an output gain control knob 48 controlling it. Optional resistor 42 pads down the output to 15–30 milliamps to insure safe output current.

Figure 8:
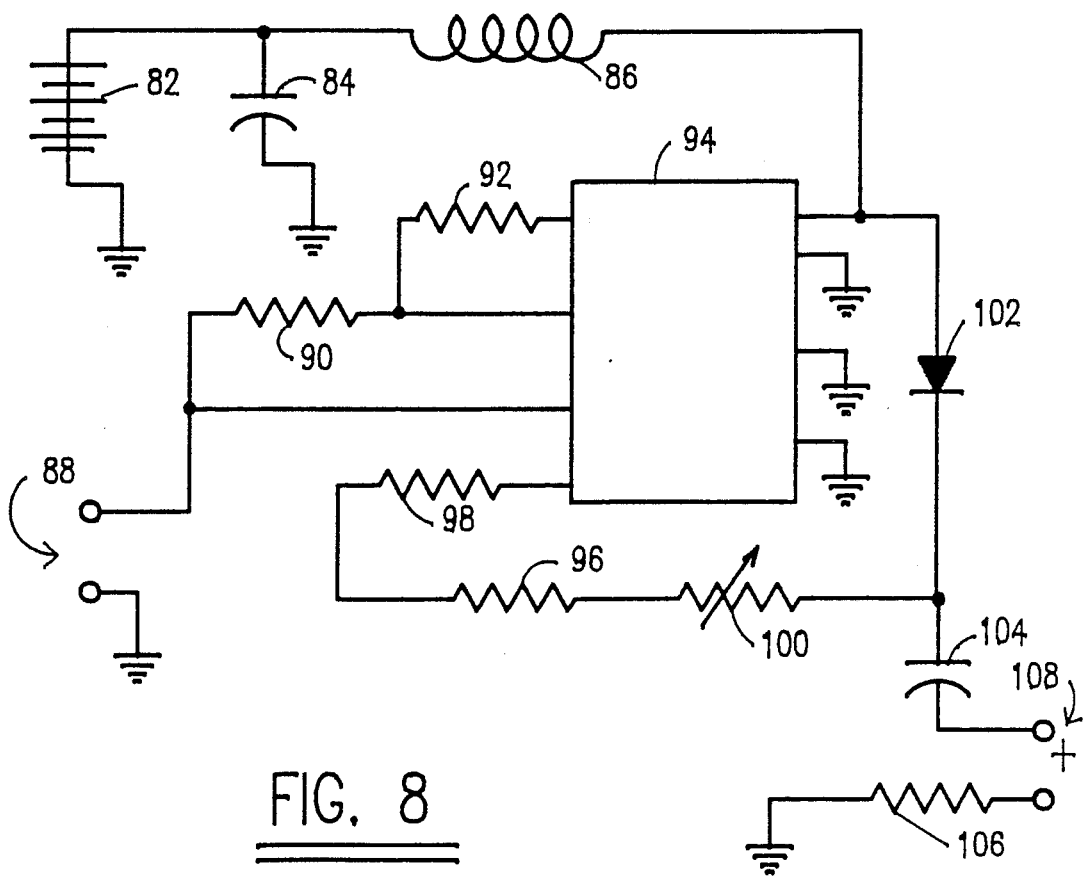
FIG. 8 is a schematic of the applicator's DC to DC converter.

A schematic circuit diagram for the DC to DC converter 36 is set forth in FIG. 8. A 9 volt battery 82 powers the converter 36. The circuit has a 1500 pf capacitor 84, and a transformer 86 to double the current. An off/on switch 88 controls current flow through a 0.5 ohm, ¼ watt resistor 90, a 180 ohm resistor 92, a microchip 94, a 27,000 ohm resistor 96, a 2,700 ohm resistor 98, a 50,000 ohm gain control 100, a diode 102 and a 3.3 micro farad (uf) capacitor 104. A 2000 ohm resistor 106 is located at the output end 108. The output will be about 2–40 volts DC and 0–50 milliamps.

The amount of flow of ionic drug through the epidermis is directly proportional to the current flow. The current generated by the iontophoresis apparatus 10 of this invention is adequate to provide penetration of drugs in an ionic form through scalp epidermis. It is the intention that this hand held apparatus 10 aid in the dilation of pores in the scalp to drive in creams containing a chemical such as minoxidil or vitamins through the scalp epidermis. No muscle stimulation is generated by apparatus 10.

In employing this apparatus 10 one must first spread a small amount of a carrier medium such as a cream containing a liquid form of a drug over the scalp area. Then after closing switch 30, placing his or her thumb on the positive electrode 18 and contacting the negative electrode 22 to the scalp, a current flow is produced sufficient to allow the drug to penetrate the scalp epidermis. Usually a five minute application is sufficient to provide a single treatment of the drug. The output current generated by this apparatus 10 is in the range of 5 to 30 milliamps. Further, apparatus 10 has no polarity.

The unique applicator head or negative electrode 22 is made from a metal foil and has a smooth round surface to prevent irritation of the scalp epidermis. The thumb electrode 18 (the positive electrode) is usually made of copper or other highly conductive metal.

The housing 12 and 14 is made of a molded plastic substance which can be easily snapped together as in a conventional plastic housing.

The battery 26 is a standard nine volt battery. However, a lessor or greater voltage can be used depending on the output desired. The capacitors 32 and 40 have a 470 microfarad capacity. The output control knob 48 is used to control the current at 1 to 10 ma per inch square. Copper wiring having a size of about number 20 is used to connect various elements of the circuit.

It is expected that the hand held apparatus 10 will have a width of about 2 inches and a length of about 6 inches with a thickness of about 1½ inches. Such a size can be conveniently held in a hand and used effectively to promote the movement of creams through a scalp epidermis.

As an alternative to the hand held apparatus set forth above, the apparatus 10a can have a plug receptacle 50 in its second end 24a for electrical connection to a plug 52 from several design variable negative electrodes.

One such electrode can be an applicator head 22a suspended from a plastic housing 23. Another negative electrode can be a comb adapter head 54 having a multiplicity of stainless steel balls 56 hanging from stainless steel wires 58 attached to a plastic housing 60. Such a comb is used to stimulate both the scalp and hair of a person with thin hair.

Another negative electrode can be a brush adapter 62 having three rows of stainless steel balls 64 suspended from stainless steel wires 66 attached to a plastic housing 68. The brush adapter is used with persons having thick hair.

A still further negative electrode can be a skull mat 70 and wire assembly 72 attached to a plastic housing 74 and in electrical connection with plug 52. This electrode is used with bald individuals to obtain maximum scalp coverage in one application. The mat 70 is made of conductive rubber.

At a first end 20a of the apparatus 10a a banana jack 76 is installed to connect a wire 78 to a contact bar 80 which acts as the positive electrode instead of the thumb electrode 18 in apparatus 10. In such an assembly, the technician applying the stimulation holds the nun conducting housing 14a and the patient holds the contact bar 80 to complete the circuit upon application of any of the electrodes to the scalp or hair.

The alternative apparatus 10a provides additional flexibility in treating a patient according to this invention. Both the scalp and hair can be stimulated at the same time by using the comb 54 or brush 62 electrodes.

Having thus described the invention, what is claimed and desired to be secured by Letters patent is:

1. An iontophoresis hand held apparatus for stimulating hair growth and increasing the absorption of an ionic form of a drug through epidermis tissue, the apparatus having a negatively charged applicator electrode and a positively charged electrode, electrically connected to a circuit enclosed within a nonconducting housing, the circuit comprising:
  a. a battery electrically connected to
  b. a DC/DC converter with a 2 volt to 40 volt output range,
  c. a 470 microfarad capacitor in electrical contact with the DC/DC converter,
  d. a load regulator resistor and a momentary switch electrically connected to the capacitor and
  e. means for connecting the circuit to the electrodes to produce a voltage differential across the electrodes.

2. The iontophoresis apparatus according to claim 1 wherein the positively charged electrode is plugged to one end of the housing and the negatively charged electrode is plugged to a second end of the housing.

3. The iontophoresis apparatus according to claim 2 wherein the negative electrode is dome shaped.

4. The iontophoresis apparatus according to claim 2 wherein the negative electrode consists of multiple stainless steel balls suspended on stainless steel wire from a plastic housing, the wire electrically connected to a plug which is plugged into the circuit at an end of the housing distal from the positively charged electrode.

5. The iontophoresis apparatus according to claim 2 wherein the negative electrode consists of a conductive rubber mat connected by a wire to a plastic housing plugged into the circuit.

6. An iontophoresis hand held apparatus for increasing the absorption of an ionic form of a drug through epidermis tissue, the apparatus having a negatively charged applicator electrode and a positively charged thumb engaging electrode mounted on an exterior surface of a housing, the housing enclosing an electrical circuit comprising;

a. a batter electrically connected to
   b. a DC/DC converter with a 2 volt to 40 volt output range,
   c. a 470 microfarad capacitor in electrical contact with the DC/DC converter,
   d. a load regulator resistor and a momentary switch electrically connected to the capacitor and
   e. means for connecting the circuit to the electrodes to produce a voltage differential across the electrodes.

7. The iontophoresis apparatus according to claim 6 wherein the battery output is 9 volts.

8. The iontophoresis apparatus according to claim 6 wherein the applicator electrode is a metal foil.

9. The iontophoresis apparatus according to claim 6 wherein the housing has a lower and upper housing component which snap together.

10. The iontophoresis apparatus according to claim 8 wherein the applicator negative electrode has a rounded smooth surface and protrudes from the housing at the end of a stem.

11. The iontophoresis apparatus according to claim 6 wherein the circuit has a first load regulator resistor and a second load regulator resistor electrically connected in series to the capacitor.

12. The iontophoresis apparatus according to claim 11 wherein the first load regulator resistor has a 3.3K to 10K ohm resistance.

13. The iontophoresis apparatus according to claim 11 wherein the second load regulator resistor has about a 50K ohm resistance and serves as a gain control.

14. The iontophoresis apparatus according to claim 6 wherein there is a first and a second 470 microfarad capacitor in electrical contact with a first and second side respectively of the DC/DC converter.

* * * * *